(12) United States Patent
Pedroni (10) Patent No.: US 7,348,579 B2
(45) Date of Patent: Mar. 25, 2008

(54) ARRANGEMENT FOR PERFORMING PROTON THERAPY

(75) Inventor: Eros Pedroni, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 373 days.

(21) Appl. No.: 11/086,462

(22) Filed: Mar. 23, 2005

(65) Prior Publication Data
US 2005/0161618 A1 Jul. 28, 2005

Related U.S. Application Data

(63) Continuation of application No. PCT/CH03/00618, filed on Sep. 15, 2003.

(30) Foreign Application Priority Data
Sep. 18, 2002 (CH) .................................... 1579/02

(51) Int. Cl.
*A61N 5/10* (2006.01)
(52) U.S. Cl. .................... 250/492.3; 315/502; 5/601

(58) Field of Classification Search ............ 250/492.3
See application file for complete search history.

(56) References Cited

U.S. PATENT DOCUMENTS 6,953,943 B2 * 10/2005 Yanagisawa et al. ..... 250/492.3

FOREIGN PATENT DOCUMENTS

| EP | 0864337 A2 | 9/1998 |
| WO | WO 01/00276 A1 | 1/2001 |

* cited by examiner

*Primary Examiner*—Robert Kim
*Assistant Examiner*—Phillip Johnston (57) ABSTRACT

A system for treating a patient by proton therapy, also called gantry, includes a proton beam guide involving, in particular, magnets, quadropoles, and the like and having an outlet aperture for guiding and directing the proton beam to the side in the patient that is to be treated. In addition, a patient table that cab en displaced in a controllable manner is provided for moving the patient into a desired position relative to the proton beam. The inventive proton beam guide and control device is mounted down from the patient table in the direction of the beam guide in a supported manner whereby being able to rotate or pivot about a horizontal axis.

9 Claims, 6 Drawing Sheets

ARRANGEMENT FOR PERFORMING PROTON THERAPY

CROSS REFERENCE TO RELATED APPLICATIONS

The present application is a continuation of international application PCT/CH03/00618, filed on Sep. 15, 2003, which designated the United States; and further claims priority to Swiss patent application 1579/02, filed Sep. 18, 2002; the both of which are herein incorporated by reference.

BACKGROUND OF THE INVENTION

The present invention relates to an arrangement for treating a patient by means of proton therapy according to the pre-characterizing clause of claim 1 as well as uses of said arrangement.

Although proton radiation therapy is advantageous particularly for the irradiation of tumors, it is still only used to a very limited extent because of high costs and the large amount of space required for such installations.

Proton therapy is nowadays preferably applied with the aid of a rotating beam delivery system, referred to as the gantry.

The system is mounted on a rotating structure and can therefore be rotated around the patient table. This configuration enables the beam to be applied sequentially to the patient (lying in his immobilization device on the patient table) from several irradiation directions.

For the treatment of deep-seated tumors using proton therapy, the required energy of the proton beam is between 70 and 250 MeV. Because of the considerable beam rigidity, the gantry requires a large amount of space (using normal magnets, the minimum deflection radius which can be applied to the beam is at least 1.3 m) and is correspondingly heavy. Gantries for photon therapy are typically 10 m long, have a diameter of 4 to 12 m and weigh up to a hundred tonnes.

A modern gantry system is expected to enable the patient table also to be rotated about the vertical axis in the horizontal plane (in addition to the axial rotation of the gantry). The aim of this is to ensure that virtually all irradiation directions to the patient lying on the table can be selected from the system (ideally a $4\pi$ solid angle). The rotation of the patient table and gantry are therefore equally justified in functional terms. The new concept of this work is to limit the rotation of the gantry to +/−90° and to utilize the full 360° rotation capability of the table for this purpose (like the latitudinal and longitudinal division of world geography). For historical reasons, this relationship has been implemented the other way round in all previous systems, i.e. rotation of the gantry through 360° and of the table only through 180° maximum.

Figure 1A:
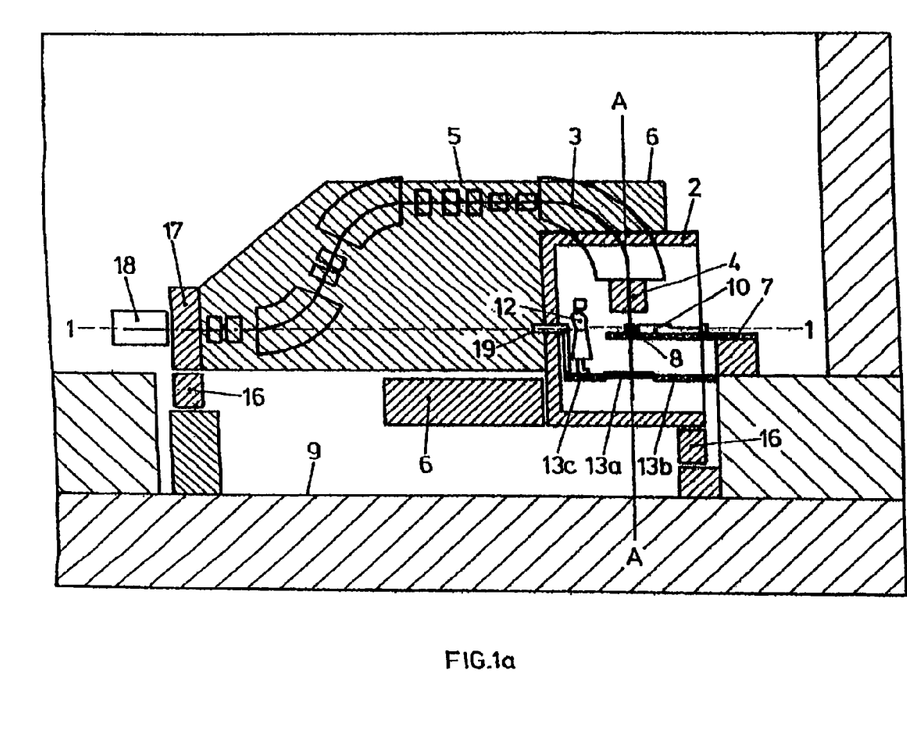
FIGS. 1a and 1b schematically illustrate a commercially available compact proton gantry with conventional mechanics, sectioned longitudinally and along the line A-A, FIGS. 2a and 2b schematically illustrate a compact proton gantry sectioned longitudinally and along the line B-B, in accordance with WO 01/00276, FIGS. 3a and 3b schematically illustrate a front-supported proton gantry arrangement according to the invention, sectioned longitudinally and along the line C-C.
Figure 1B:
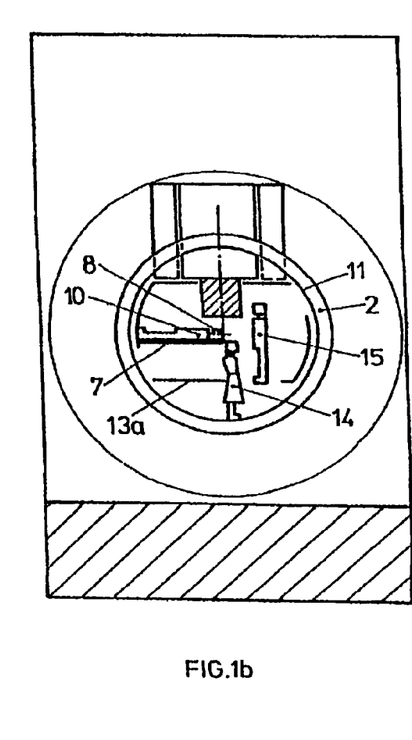

Today's commercially available systems are based on the concept that the gantry can be rotated completely through 360° about the longitudinal beam axis. The principle of a conventional system of this kind will now be described schematically and in detail with reference to FIG. 1.

The Paul Scherrer Institute has already made a significant contribution to the development of proton therapy. PSI's Gantry 1 is the world's second oldest photon gantry after Loma Linda in California. In operation since 1996, it is still the only gantry employing dynamic beam-scanning. It remains the gantry with the smallest diameter anywhere (4 m). A number of features derived from the PSI system have already been used in modified form for industrial patents.

Such systems are described, for example, in the two European patents EP 0 911 964 and EP 0 864 337.

Experience with the present system has shown us the importance of good accessibility to the patient table in each radiation phase.

Figure 2A:
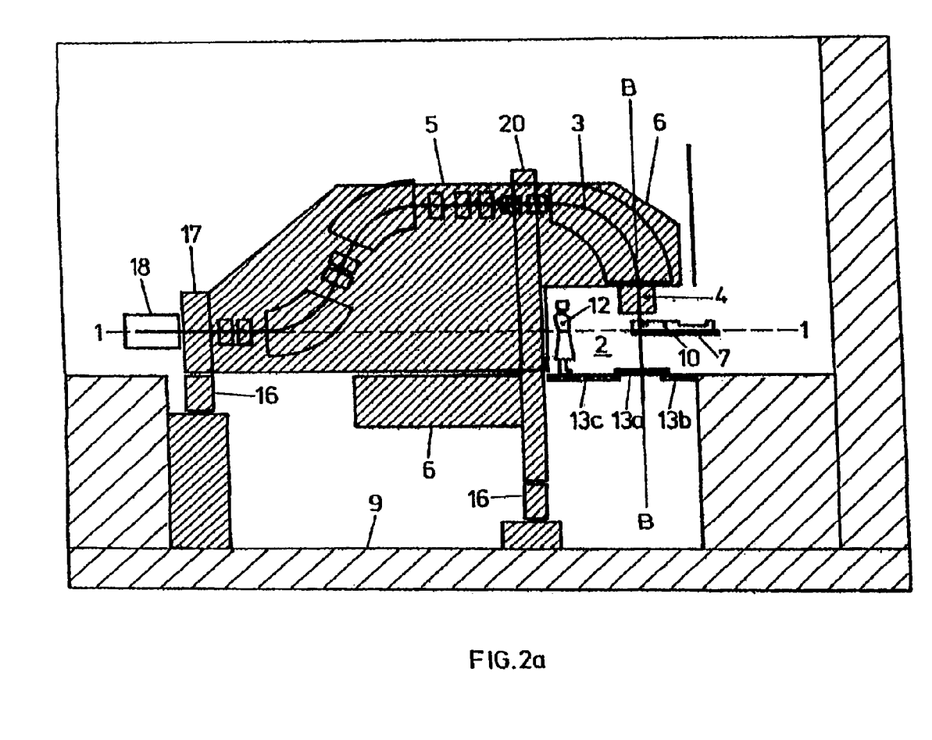
Figure 2B:
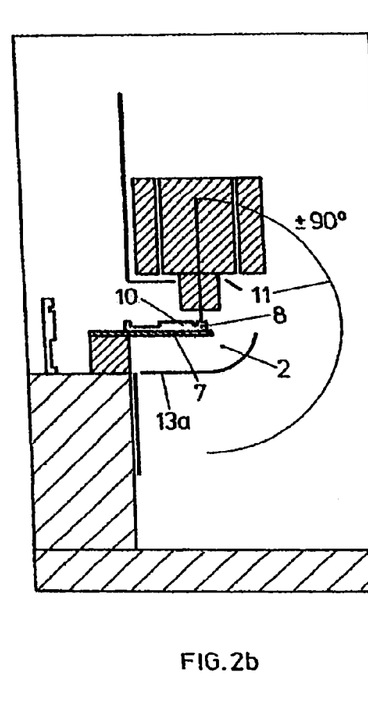

International patent application WO 01/00276 on this subject from the year 2000 (priority 1999) describes a device for performing proton therapy wherein the proton beam guiding and controlling device is implemented so that it can pivot or rotate only through a maximum angle of 270°, so that, as required, good accessibility to the patient table is ensured in each phase of radiation. WO 01/00276 will not be described in detail here, but a proton radiation arrangement similar to WO 01/00276 will be described schematically in further detail with reference to FIG. 2.

Although the requirement for accessibility to the patient table is met in the arrangement according to WO 01/00276, the requirement for dimensional reduction and simplification of the gantry remains. One object of the present invention is therefore to propose a different arrangement for performing proton therapy which, on the one hand, ensures continuous accessibility to the patient table without penalties in terms of functionality and, on the other, allows further simplification and increased accuracy in performing proton therapy, as well as in particular a further reduction in the dimensions of gantry components and of the gantry itself.

This object is achieved according to the invention primarily by means of an arrangement as set forth in claim 1.

SUMMARY OF THE INVENTION

According to the invention it is proposed that the proton beam guiding and controlling device, hereinafter referred to as the gantry, is mounted downstream of the patient table in the beam guiding direction and is supported in a rotatable or pivotable manner about a horizontal axis, the essential feature remaining that at all times the patient table is accessible and the patient can be attended to from one side.

According to a preferred embodiment variant, the inventive arrangement or gantry is pivotally mounted via a small roller at its frontmost point, the gantry being disposed so that it can pivot or rotate upward and downward through up to 135° in each case from a horizontal plane, essentially running through the axis of rotation, similarly to the implementation according to WO 01/00276. Obviously, the total angle of 270° mentioned can also be selected smaller, depending on the design of the gantry, but must not be less than ±90° from the horizontal plane or 180° in total.

An advantage of the proposed arrangement according to the invention is that at least part of the cabling can be connected from the front of the gantry, which allows a clean, local separation of the cable runs for measurement signals and monitoring sensors from the magnetic feed. This eliminates any interference between the signals, thereby also enabling the proton beam guiding accuracy to be increased, as the sensitive measurement devices are unaffected by the magnetic feeds.

According to another embodiment variant, the heavy part of the proton beam guiding and control unit or gantry, such as the 90° magnet, is concealed so that only the nozzle of the proton beam is visible to the patient. The term "nozzle" denotes the housing and the radiation apparatus contained therein at the beam exit of the gantry immediately in front of the patient. Also located there are e.g. the measuring systems for monitoring the beam (measurement of the beam position and intensity), the range modulator, laser and TV cameras for positioning the patient and adjusting the beam, etc. This part is visible to the patient. On the other hand, the heavy part with the 90° magnet, which can weigh as much as 20 t and may have recesses 2 m high and 1 m wide or more, can be well concealed in the present arrangement by implementing the radiation chamber, according to a further embodiment variant, as a semi-open space, e.g. the size of a room, the lateral wall being absent from the accessibility side only.

The main advantages of the proposed arrangement according to the invention are as follows:

The configuration of the radiation chamber is simpler;
The costs and complexity for implementing a movable auxiliary floor are eliminated;
The patient table is accessible at all times;
Smaller dimensioning of the gantry is possible, or the pit below the patient table can be made less deep.
Simpler and cheaper system;
Higher reliability and accuracy;
Smaller diameter of the system or rolling device by mounting of the front roller
The new arrangement is suitable not only for centric systems as described in WO 01/00276 but also for eccentric systems (gantry) like the present system (gantry) of the Paul Scherrer Institute (PSI).

Other preferred embodiment variants of the arrangement according to the invention are set forth in the dependent claims.

The arrangement according to the invention is particularly suitable for treating a patient using proton therapy, a person lying on the patient table being positioned by moving the patient table and proton beam delivery system (gantry) in such a way that the proton beam can irradiate the site to be treated in the patient's body from any desired direction and that the patient table remains accessible from one side at all times.

BRIEF DESCRIPTION OF THE SEVERAL VIEWS OF THE DRAWINGS

The invention will now be explained in greater detail using examples and with reference to the accompanying drawings, in which.

DETAILED DESCRIPTION OF THE INVENTION

To facilitate understanding of the present invention, a currently commercially available system based on the concept that the proton beam system or gantry can be rotated completely through 360° about the longitudinal beam axis will first be described schematically with reference to FIGS. 1a and 1b.

A patient 10 is treated in a cylindrical chamber, the radiation chamber 2. The gantry 3 is installed outside the chamber. Only the last part, the so-called nozzle 4, with the measuring equipment for checking the spatial distribution of the dose, extends into the chamber (the patient must be able to be placed as near as possible to the nozzle).

The whole arrangement is carried by a rotating structure 5, including the counterweight 6 of the gantry. Item 16 shows the position of the wheels 16 on which the gantry rotates via two rollers. The rear roller 17 can be kept relatively small with a radius of approximately 1 m. The front roller is the radiation chamber itself. Item 18 shows the cable drum where the gantry cabling is connected.

The patient table 7 is used to position the patient in the isocenter 8 of the machine (isocenter=point of impact of the beam during gantry rotation). Because the radiation chamber and nozzle rotate together with the gantry, the table is anchored directly in front of the chamber. The table top with the patient lying thereon extends from outside into the chamber.

The medical requirement that the patient table be rotatable around the tumor in the horizontal plane (in the isocenter of the machine—about the A-A axis according to FIG. 1a) means that the inner radius 11 of the cylindrical radiation chamber shall be at least 2 m (length of the human body). In order to clearly illustrate the rotation and the space requirement necessary for that purpose for head irradiation, the patient 10 in FIG. 1 has been drawn in a front and side elevation perpendicular to the point of observation in each case.

The height of the patient table surface 7 above the floor of the radiation chamber is therefore also fixed at approximately 2 m. Without additional equipment, access by personnel 12 to the patient in the irradiation position is thus unsatisfactory. The need for a flat false floor 13 inside the chamber is highlighted in the front view in FIG. 1 where the position of the assistant with 15 and without 14 an auxiliary floor of this kind is illustrated.

The construction of a flat floor 13 inside the cylindrical radiation chamber is rather complicated for various reasons.

If the beam is applied from below, the false floor must open and match the rotation of the nozzle (movable part of the cover for the nozzle 13a). Also the remaining parts of the floor, part behind 13c and part in front of 13b, cannot be anchored directly into the chamber because the radiation chamber rotates with the gantry but the floor is designed to remain horizontal.

The front part 13b of the floor can be supported from outside the chamber. However, the main problem is in the rear part of the chamber, in part 13c, which is "cut off" by the movement of the nozzle. The problem can be solved here using a built-in counter-rotation 19 to the rotation of the gantry in the rear part of the chamber, according to the principle used for installing the patient table in the PSI's Gantry 1.

This idea (of counter-rotation) has been subsequently adopted for supporting the false floor. Commercial systems currently in existence all have either no floor in the cylindrical chamber or a floor which is constructed according to the principle outlined above (rear support with counter-rotation, front support fixed).

Although a movable floor inside the cylindrical radiation chamber is feasible, it is certainly neither cheap nor easy.

The object of WO 01/00276 of the PSI was to offer a better solution ensuring better accessibility to the patient table, without penalties in terms of functionality, and with the floor 13b and 13c installed in a fixed manner without counter-rotation.

FIGS. 2a and 2b schematically illustrate the gantry arrangement proposed in WO 01/00276 sectioned longitudinally and along the line B-B. It should be noted that FIGS. 2a and 2b employ the same reference characters to denote the corresponding parts in FIGS. 1a and 1b.

The difference between the gantry described in FIGS. 2a and 2b and the corresponding system shown in FIGS. 1a and 1b is primarily that the rotation of the gantry is limited to ±90° (+180°, −120°) in the vertical plane on one side of the gantry only. This is particularly evident from the illustration according to FIG. 2b. The non-settable angles of the gantry are selected mirror-symmetrically and achieved using rotation of the patient table through 180° in the horizontal plane. In principle, if the rotation of the table in the horizontal plane is fully available, no limitations in the selection of the irradiation direction are likely at least theoretically. The space gained on the opposite side of the gantry can therefore be utilized for the fixed installation of the patient table 7 and of the fixed floor 13 in the hole of the pit. FIGS. 2a and 2b likewise clearly illustrate that accessibility to the patient table is provided in a much easier and better manner compared to the arrangement shown in FIGS. 1a and 1b.

However, as is also evident from FIG. 2a, the system is very large because of the use of the large rotating disk 20 and requires a large amount of space. The approximately 7 m rotating disk is difficult to construct and to transport. The required precision of the isocenter of better than 1 mm is correspondingly difficult to implement. It should additionally be noted that the wheels 16 in FIG. 2 are below the large roller 20 and therefore the pit is made deeper than that shown in FIGS. 1a and 1b.

Figure 3A:
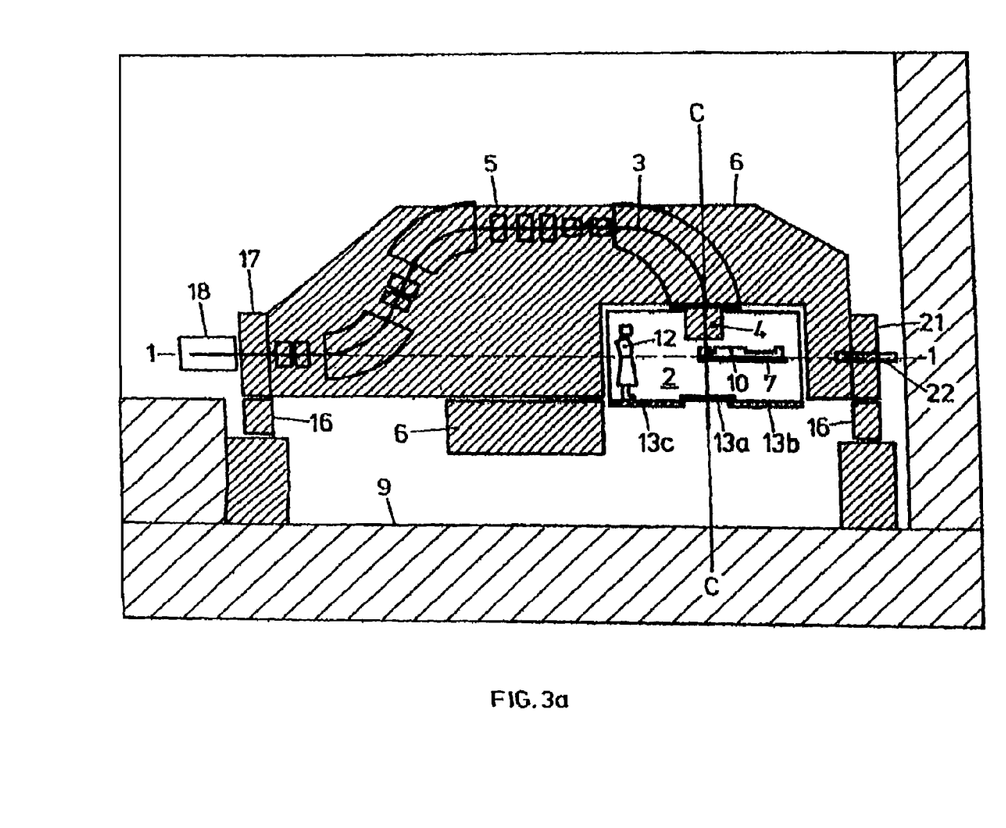
Figure 3B:
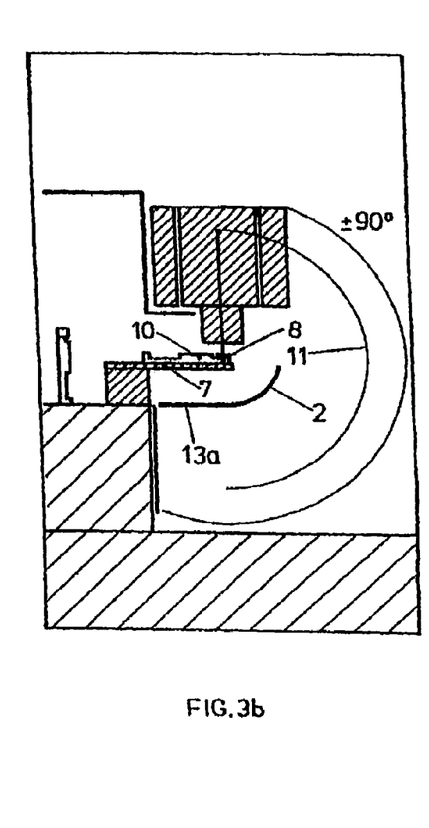

In order to further simplify the system, the inventive arrangement schematically illustrated in FIGS. 3a and 3b has now been selected. The basic idea of the newly developed gantry consists in supporting the radiation unit or gantry only after the radiation chamber using a small roller 21. This obviates the need for the correspondingly large-diameter rotating disk shown in FIG. 2a. The other features of the arrangement according to FIGS. 2a and 2b are essentially retained in the new concept. FIG. 3a schematically illustrates the inventive arrangement sectioned longitudinally and FIG. 3b shows a cross-section along the line C-C. It now becomes clear that the gantry 3 is rotatable in a laterally limited manner similar to the arrangement shown in FIGS. 2a and 2b. The radiation chamber 2 is in turn accessible from one side of the gantry. The radiation chamber 2 is preferably a semi-open space the size of a room, measuring approximately 4.5 m long, approximately 4 m deep from the side and approximately 2.2 to 2.5 m high. For the patient, only the final element of the proton beam delivery system or nozzle is visible, the heavy part of the gantry such as the 90° magnet being concealed. The floor is installed in a fixed manner in the areas 13c and 13b similar to FIGS. 2a and 2b apart from a slit (approximately 50 cm wide) for guiding the nozzle. This area can be covered e.g. using a bilateral rolling cover (13a). As already mentioned above, the clear advantages of the arrangement according to the invention lie in the following features:

Probably the greatest advantage of this arrangement is that the manufacturing costs of the large roller 20 from FIG. 2 are eliminated by supporting the gantry via a small roller at its frontmost position and the associated rotation.

In addition, the advantages of this solution remain the good accessibility to the patient table with an almost exclusively fixed floor.

The space around the patient table is large and can be conveniently configured, it also being possible to install further equipment on the fixed floor within range of the table, such as an anesthetics table, a computer tomograph (CT), a positron emission tomograph (PET), etc.

At least part of the cabling can be connected at the front of the gantry. This allows a clean, local separation of the cable runs for measurement signals or monitoring sensors from the magnetic feed.

The arrangement permits a space-saving design of the access labyrinth or shielding configuration.

The shielding on the walls of the radiation chamber can be reduced wherever these face away from the gantry.

Figure 5:
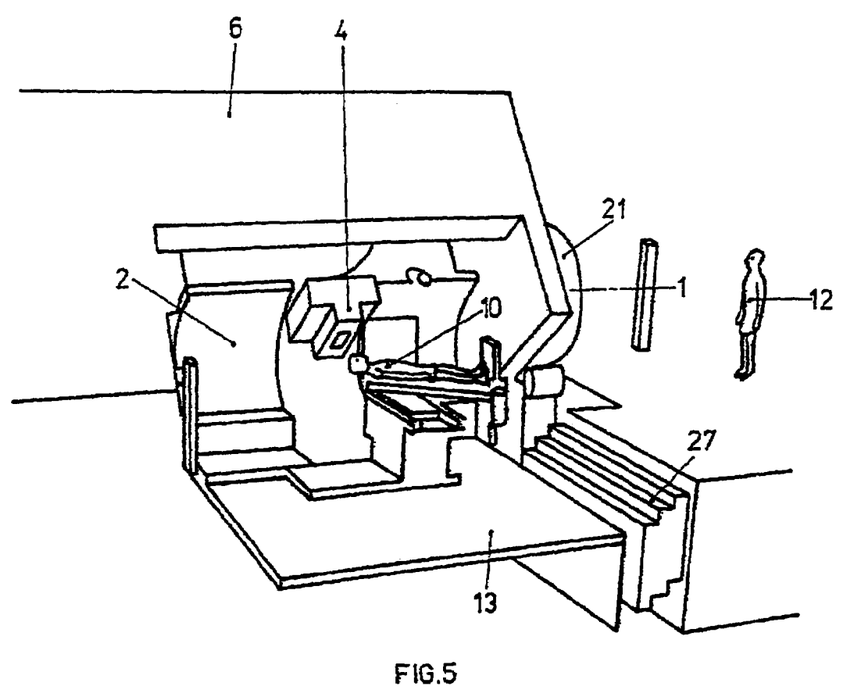
FIG. 5 is a lateral perspective view of an eccentric gantry according to the invention, and FIGS. 6a thru 6c schematically illustrate another embodiment variant of a proton gantry arrangement according to the invention, sectioned longitudinally and along the lines C-C and D-D.

A further advantage of the new concept is that it can be used not only for centric compact systems, as shown in FIGS. 2a and 2b, but also for eccentric compact systems as shown in FIG. 5, for example. However, because of the eccentricity the radiation chamber must be suspended on the gantry e.g. in the sense of a counterweight and kept horizontal with the aid of the counter-rotation.

Moreover, conceptually the new solution is generally more flexible than the solution shown in FIGS. 2a and 2b. Whereas the latter is only possible for a more compact gantry, the new system can be used both for compact, compact-eccentric and for "long throw gantries" as well as for beam application using scanning or scattering technologies. The large variability is attractive for commercial use, particularly if customer-oriented solutions are to be offered.

Figure 4:
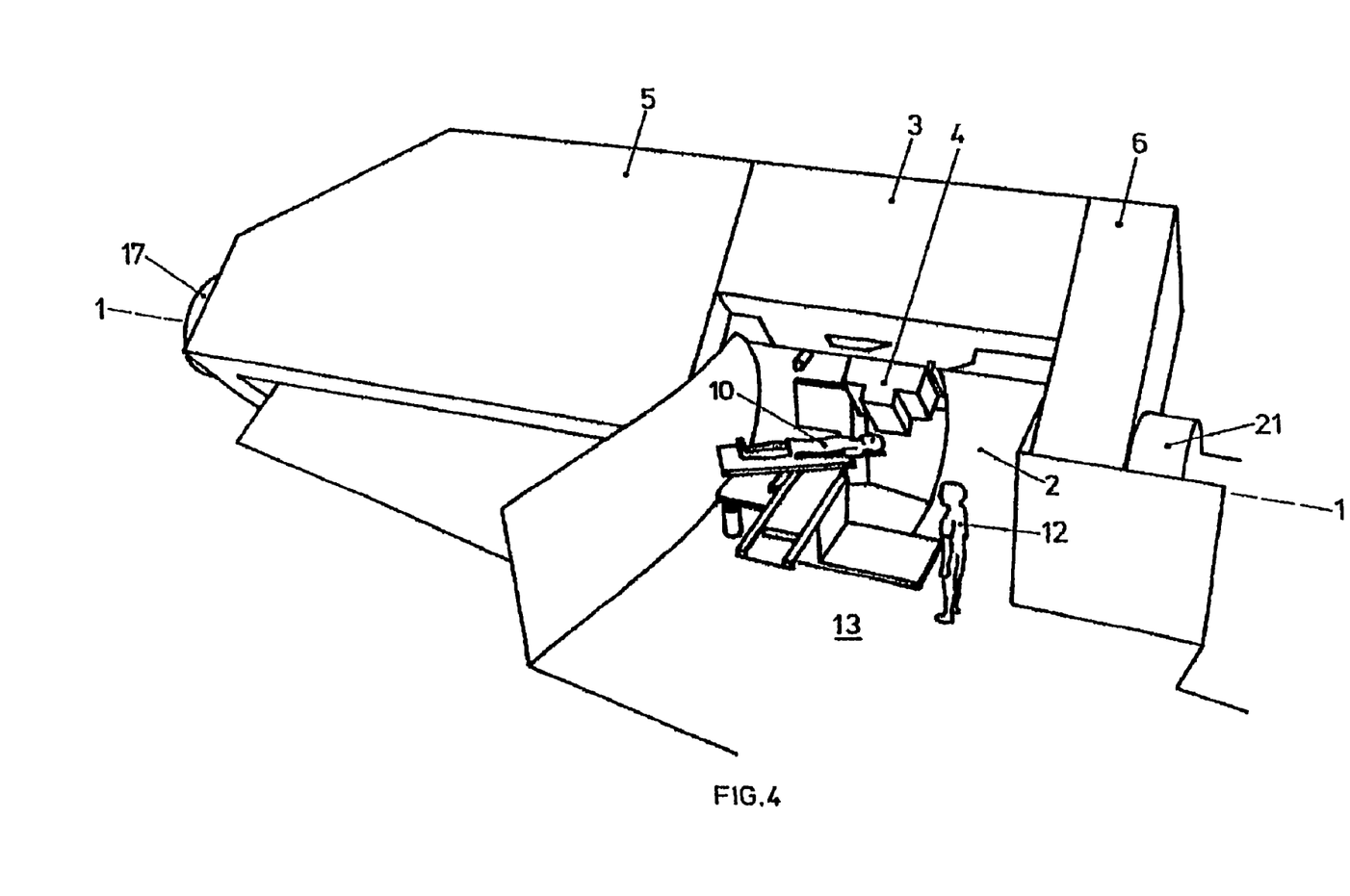
FIG. 4 is a lateral perspective view of a centric gantry according to the invention.

FIGS. 4 and 5 illustrate by means of perspective views the use of the arrangement according to the invention both in a compact centric system and also in an eccentric compact gantry system.

FIG. 4 is a perspective view of a centric gantry pivoted about the axis of rotation 1 via the two rollers 17 and 21, radiation being applied from the top right (viewed from the patient).

The arrangement is called centric because the gantry is rotatable around the radiation chamber 2 disposed in a rigid or fixed manner whereby the chamber floor 13 is fixed.

In contrast, in the arrangement according to FIG. 5 the radiation chamber is pivoted eccentrically in a circular motion about the axis of rotation 1, the patient table 10 obviously having to perform a corresponding movement depending on the radiation position. In this case radiation is applied from top left. In order to ensure the accessibility of the chamber floor 13 for an attendant 12, a movable e.g. stepped access 27 is necessary. For example, if the radiation is applied in the horizontal direction, the need for the steps 27 is eliminated, as the chamber floor 13 is on the same level as the surrounding area. However, if the radiation is applied from below, the chamber floor 13 is elevated accordingly and is therefore above the level of the surrounding area.

Figure 6A:
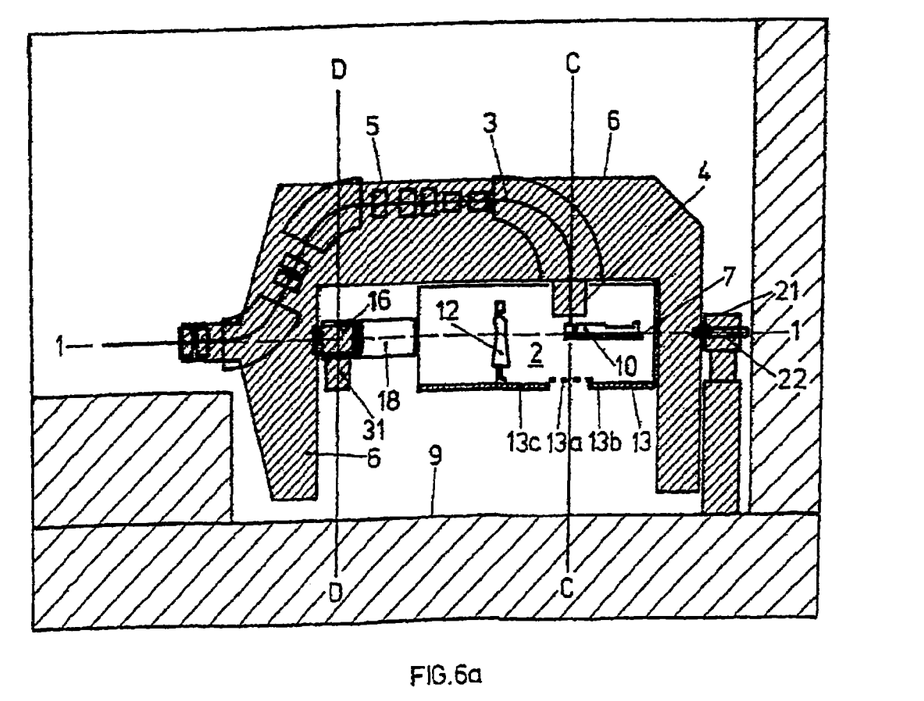
Figure 6B:
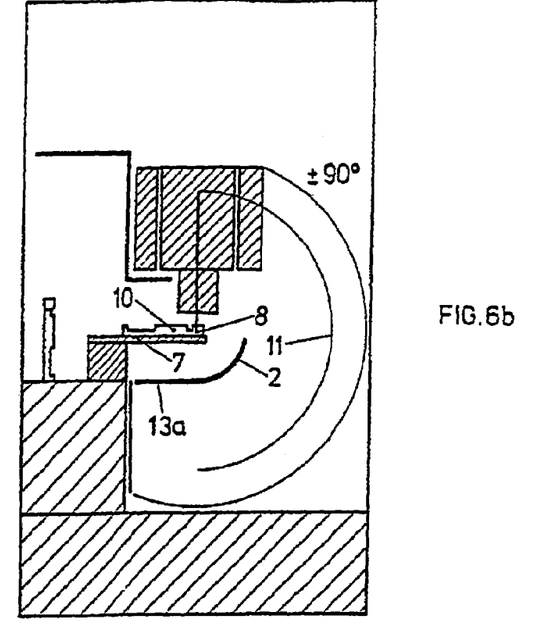
Figure 6C:
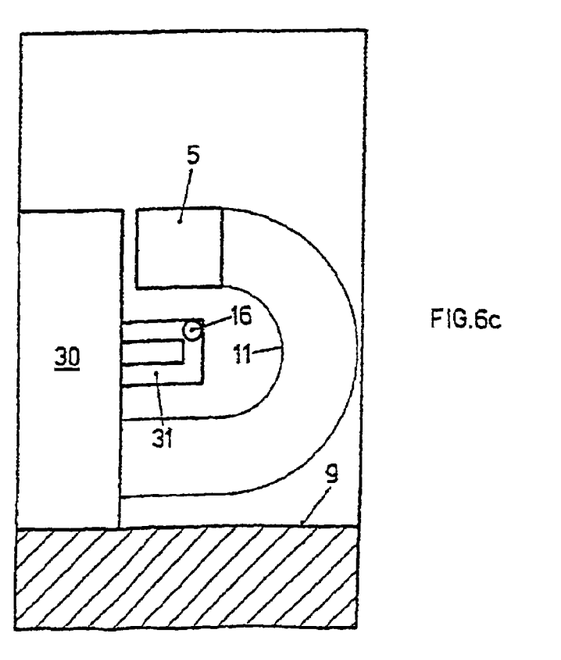

FIGS. 6a and 6b show another embodiment variant of a gantry arrangement or system according to the invention. The system illustrated in FIGS. 6a and 6b differs from that shown in FIGS. 3a and 3b in that the rear support of the gantry is not positioned at the end, but is oriented toward the interior or toward the radiation room 2. Otherwise, the gantry in FIG. 6a corresponds to that in FIG. 3a, as does the section along the line C-C shown in FIG. 6b. On the other hand, FIG. 6c shows the section along the line D-D, i.e. the rear support of the gantry, the rear wheel 16 being supported laterally on the rear chamber wall 50 via an e.g. U-shaped frame 31, i.e. the support is provided on the chamber floor 9, unlike in FIG. 3*a*. It is accordingly possible to implement the cable drum 18 in the central area of the gantry. The way the gantry is supported, as shown in FIGS. 6*a* to 6*c*, shortens the structure and because of the shorter distance between rear and front roller 16, better stability is achieved, i.e. there is less risk of sagging. The other advantages, as described with reference to FIGS. 3*a* and 3*b*, are of course retained in the arrangement according to FIGS. 6*a* to 6*c*.

The representations in FIGS. 1 to 6 are of course merely examples used to explain the present invention in more detail.

It is self-evidently possible to adapt the proton radiation arrangement in any number of ways, to modify it or to supplement it with further elements. Particular reference is made to WO 01/00276 whose content is an integral part of the present invention, and whose specific embodiments, likewise in combination with the features defined according to the invention, are part and parcel of the present invention.

The invention claimed is:

1. An arrangement for treating a patient by means of proton therapy, comprising:
    a proton beam delivery system including magnets, quadrupoles, and an exit window, the proton beam delivery system arranged to guide or direct a proton beam from a proton beam source to a location in the patient that is to be treated;
    a radiation chamber;
    a patient table within the radiation chamber, arranged, in a substantially horizontal plane and controllable so as to move the patient into a desired position relative to the proton beam entering the radiation chamber via the exit window, and
    a proton beam guiding and controlling device mounted on a first support and a second support to pivot about a horizontal axis, wherein the radiation chamber is positioned between the first support and the second support, wherein the chamber floor is installed in a fixed manner without counter-rotation, and wherein the horizontal axis extends substantially within the horizontal plane in which the patient table is arranged.

2. The arrangement according to claim 1, wherein the first support is located proximal to the proton beam source, wherein the second support is located distal to the proton beam source, and wherein the second support includes a roller.

3. The arrangement according to claim 1, wherein the proton beam guiding and controlling device is arranged so as to pivot up or down through at least 135° from the horizontal plane.

4. The arrangement according to claim 1, wherein the proton beam guiding and controlling device is arranged such that it can be rotated about an axis of rotation from a vertical plane through an angle of about 90°, essentially running through an axis of rotation, from a side of the vertical plane on which the patient is disposed up to an angle of approximately 180° on the opposite side of the vertical plane.

5. The arrangement according to claim 1, wherein radiation chamber has at least a semi-open space with at least one side wall extending away from a side from which the patient table is accessible.

6. The arrangement according to claim 1, wherein the radiation chamber is arranged such that the magnet or a last magnet of the beam guide is not visible from the radiation chamber such that for the patient only a nozzle is visible by disposing a slit in the radiation chamber wall, the nozzle moving along a slit opening in the radiation chamber wall, and a bilateral cover is provided on the slit, the cover being a rolling cover.

7. The arrangement according to claim 1, wherein the patient table is arranged so as to be rotationally and translationally movable such that when combined with rotation of the proton beam guiding and controlling device any site in the patient's body can be irradiated.

8. The arrangement according to claim 7, wherein mechanics for moving the patient table are not disposed in a region of the proton beam.

9. The arrangement according to claim 1, further comprising cabling for at least one of measurements signals sensors for monitoring the patient's condition, at least part of the cabling being routed or connected from a front through an area of a roller of the first support in order to allow local separation from a magnetic feed.

* * * * *